United States Patent

Feit et al.

[11] 3,950,376
[45] Apr. 13, 1976

[54] SULFAMYLBENZOIC ACID DERIVATIVES

[75] Inventors: Peter Werner Feit, Gentofte; Ole Bent Tvaermose Nielsen, Vanlose; Herta Bruun, Graested, all of Denmark

[73] Assignee: Leo Pharmaceutical Products Ltd. A/S, Ballerup, Denmark

[22] Filed: June 18, 1973

[21] Appl. No.: 370,609

[30] Foreign Application Priority Data
July 13, 1972 United Kingdom.............. 32909/72
Nov. 7, 1972 United Kingdom.............. 51384/72
Jan. 24, 1973 United Kingdom.............. 3658/73

[52] U.S. Cl............... 260/415 D; 260/294.8 G; 260/294.8 R; 260/306.8 R; 260/309; 260/332.2 A; 260/347.2; 260/470; 260/501.12; 260/516; 260/519; 424/263; 424/270; 424/273; 424/275; 424/285; 424/304; 424/310; 424/316; 424/319
[51] Int. Cl.[2].................................. C07C 143/78
[58] Field of Search ........ 260/465 D, 470, 516, 519

[56] References Cited
UNITED STATES PATENTS

| | | | |
|---|---|---|---|
| 3,634,583 | 1/1972 | Feit................................ | 260/519 X |
| 3,706,790 | 12/1972 | Sprague et al..................... | 260/465 |
| 3,806,534 | 4/1974 | Feit................................ | 260/519 X |

*Primary Examiner*—Elbert L. Roberts
*Assistant Examiner*—Dolph H. Torrence
*Attorney, Agent, or Firm*—Jackson, Jackson & Chovanes

[57] ABSTRACT

Compounds of the general formula

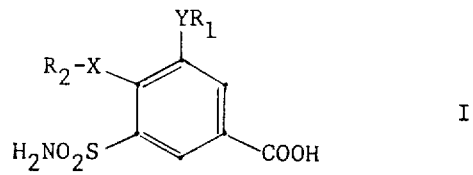

I in which $R_1$ represents a straight or branched $C_1$-$C_6$ alkyl, alkenyl or alkynyl radical, or a $C_1$-$C_3$ alkyl radical substituted with phenyl, halophenyl, trifluoromethylphenyl, (lower alkoxy)phenyl, or with a 5-membered or 6-membered heterocyclic ring containing not more than two heteroatoms selected from the group consisting of oxygen, sulphur and nitrogen; $R_2$ stands for a phenyl radical, optionally being substituted with halogen, lower alkyl, hydroxy, or lower alkoxy; X and Y stand for oxygen or sulphur; their salts and esters and methods for their preparation.

The compounds of the invention possess an outstanding diuretic and saluretic activity with a very low excretion of potassium ions and a low toxicity.

25 Claims, No Drawings

SULFAMYLBENZOIC ACID DERIVATIVES

This invention relates to a series of new compounds, their salts and esters and to methods for the preparation of the compounds having the formula:

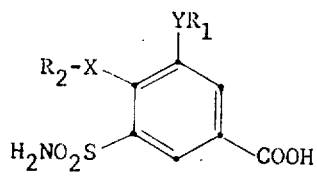

in which $R_1$ represents a straight or branched $C_1$–$C_6$ alkyl, alkenyl or alkynyl radical, or a $C_1$–$C_3$ alkyl radical substituted with phenyl, halophenyl, trifluoromethylphenyl, (lower alkoxy)phenyl, or with a 5-membered or 6-membered heterocyclic ring containing not more than two heteroatoms selected from the group consisting of oxygen, sulphur and nitrogen; $R_2$ stands for a phenyl radical, optionally being substituted with halogen, lower alkyl, hydroxy, or lower alkoxy; X and Y stand for oxygen or sulphur.

In particular, $R_1$ may represent e.g. a methyl, ethyl, propyl, isopropyl, butyl, isobutyl or tert. butyl radical, or one of the different isomeric pentyl, or hexyl radicals, an alkenyl or alkynyl radical, e.g. an allyl, or propargyl radical, a benzyl or phenethyl radical, a 2-, 3-, or 4-pyridylmethyl, 2- or 3-furylmethyl, 2- or 3-thienylmethyl, thiazolylmethyl, or imidazolylmethyl radical; or one of the corresponding ethyl radicals.

Of particular value are the compounds of the invention in which $R_1$ is selected from the group consisting of straight or branched $C_3$–$C_5$ alkyl radicals, and a methyl radical being substituted with phenyl, furyl, thienyl, and pyridyl, and the correspondingly substituted ethyl radicals.

The substituents $R_1$ and $R_2$ of formula I can be further substituted in different positions with different groups, such as one or more halogen atoms, e.g. chlorine or bromine atoms, lower alkyl, halo-lower alkyl, e.g. trifluoromethyl; hydroxy groups, which may be etherified, e.g. lower alkoxy, such as methoxy, ethoxy, n-propoxy, isopropoxy, n-butoxy or isobutoxy, or esterified with lower aliphatic carboxylic acids, such as lower alkanoic acids, e.g. acetic, propionic or pivalic acid, lower alkenoic acids, e.g. acrylic or methacrylic acid, or with lower aliphatic dicarboxylic acids, e.g. oxalic, malonic, succinic, glutaric, adipic, maleic or fumaric acid or their acid esters with lower alkanols, e.g. methanol or ethanol; or etherified mercapto groups such as methylthio, ethylthio, isopropylthio, butylthio or isobutylthio radicals.

Whenever the expression "lower alkyl" is used in the foregoing and in the following it stands for a straight or branched alkyl radical with from 1 to 6 carbon atoms in the chain.

The salts of the compounds of the invention are pharmaceutically acceptable salts, and include, for example, alkali metal salts, alkaline earth metal salts, the ammonium salt or amine salts formed, for instance, from mono-, di- or trialkanolamines or cyclic amines. The esters of the compounds are preferably derived from lower aliphatic alcohols, cyanomethanol and benzyl alcohol.

It has surprisingly been found that the compounds of the invention possess an outstanding diuretic and saluretic activity with a very low excretion of potassium ions and a low toxicity which makes the present compounds particularly valuable in human or veterinary practice.

In the present series of compounds, the position of the $YR_1$ group is essential, as according to experiments performed in connection with the present invention, it has been found that the compounds of the following formula

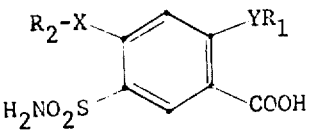

in which $R_1$, $R_2$, X and Y have the above meaning, and in which the $YR_1$ group is placed in the 2-position have a negligible diuretic effect.

The compounds of the invention are more stable than the known benzoic acid derivatives containing an amino or substituted amino group, e.g. furosemide, which are light-sensitive and must be stored in dark receptacles.

Further the compounds of the invention are also extremely valuable in the treatment of patients suffering from hypersensitivity towards sulfanilamide diuretics and metanilamide diuretics because there exists no cross hypersensitivity between these compounds and the compounds of the invention.

The present compounds are effective after oral, enteral or parenteral administration, and are preferably prescribed in the form of tablets, pills, dragees, or capsules containing the free acid or salts thereof with atoxic bases, or the esters thereof, mixed with carriers and/or auxiliary agents.

Salts, which are soluble in water, may with advantage be administered by injection. The parenteral preparations are in particular useful in the treatment of conditions in which a quick dehydration is desirable, e.g. in the intensive therapy in the case of oedemas in the lung. In the continuous therapy of patients suffering from e.g. hypertension, the tablets or capsules may be the appropriate form of pharmaceutical preparation owing to the prolonged effect obtained when the drug is given orally, in particular in the form of sustained-release tablets.

In the treatment of heart failure and hypertension such tablets may advantageously contain other active components, as specified below.

Another object of the invention resides in the selection of a dose of one of the compounds of the invention or their salts or esters which can be administered so that the desired activity is achieved without simultaneous secondary effects. In such a dosage unit the compounds are conveniently administered as a pharmaceutical preparation containing from 0.1 mg to 25 mg of the active compound. The compounds of formula I are preferably administered in amounts from 0.25 mg to 10 mg. By the term "dosage unit" is meant a unitary, i.e. a single dose capable of being administered to a patient, and which may be readily handled and packed, remaining as a physically stable unit dose, comprising either the active material as such or in a mixture of it with a pharmaceutical carrier and auxiliary agents.

In the form of a dosage unit the compounds may be administered one or more times a day at appropriate intervals. The daily dose usually amounts to from 0.5 to 50 mg always depending, however, on the condition of the patients and according to the prescription of the medical practitioner.

In pharmaceutical compositions containing the compounds of the invention, organic or inorganic, solid or liquid carriers suitable for oral, enteral, or parental administration can be used to make up the composition. Gelatine, lactose, starch, magnesium stearate, talc, vegetable and animal fats and oils, gum, polyalkylene glycol, or other known carriers for medicaments are all suitable as carriers.

In the pharmaceutical compositions, the proportion of therapeutically active material to carrier substances can vary between 0.2 percent and 90 percent.

The compositions may further contain other therapeutic compounds applied in the treatment of, for example oedemas and hypertension, besides the well-known auxiliary agents. Such other compounds may be, for instance, Veratrum- or Rauwolfia alkaloids, e.g. reserpine, rescinnamine or protoveratrine or synthetic hypotensive compounds, e.g. hydralazine, or other diuretics and saluretics, such as the well-known benzothiadiazines, e.g. hydroflumethiazide, bendroflumethiazide, and the like. Potassium-sparing diuretics, e.g. triamterene, may also be used in the preparation of the compositions. For some purposes it may be desirable to add small amounts of aldosterone antagonists, e.g. spironolactone.

It is another object of the invention to provide methods of preparing the compounds of the invention.

The compounds of the invention may be prepared by various methods, for example according to the following reaction scheme:

erably be about the boiling point of the solvent.

If desired, an ester of a compound of the formula II can be used in the reactions, whereby the compound of the formula I is obtained as an ester. The corresponding free acid may, optionally, be obtained by a subsequent saponification. In case of the desired product being an ester and the starting material of formula II being the free acid, an esterification can be performed either before or after the alkylation process.

The starting materials of the formula II are new and interesting compounds which also possess valuable diuretic and saluretic activities.

The compounds of formula II (Y=S) may be prepared from a3-amino-4-halo-5-sulphamylbenzoic acid, which compounds are known or can be produced analogous with the known ones, by diazotation and subsequent treatment with sodium sulfide, whereby a 5,5'-dicarboxy-2,2'-dihalo-3,3'-disulphamyl-diphenyl disulfide is produced. This compound is then reduced to 3-mercapto-4-halo-5-sulphamylbenzoic acid, for instance by using zinc in glacial acetic acid. The resulting mercapto compound thereafter is alkylated to the desired starting material of the formula II (Y=S).

As generally known for the transformation of aromatic amines to the corresponding hydroxy compounds, the starting materials of formula II in which Y stands for oxygen can be produced from the above 3-amino-4-halo-5-sulphamylbenzoic acids by diazotation and subsequent replacement of the diazonium group in the 3-position by a hydroxy group.

The compound thus obtained can under conditions analogous to those described above for the corresponding mercapto derivatives be alkylated to the starting materials of formula II (Y=O).

Appropriately the alkylation can be performed either on the free acid of formula II or on one of its esters by

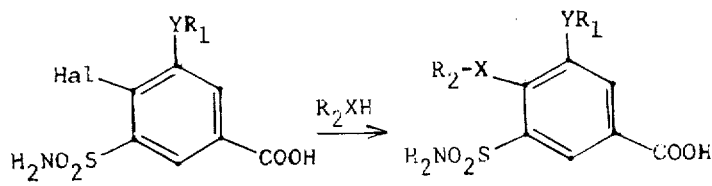

II        I in which formulae the substituents $R_1$, $R_2$, X, and Y are as defined before, and Hal stands for a halogen atom, preferably chlorine or fluorine.

The reaction between a compound of the formula II and a compound $R_2XH$, in which X and $R_2$ have the above meaning, is effected by heating the components in the presence of an acid binding agent, in a suitable solvent or, when appropriate by using the compound $R_2XH$ as solvent. The temperature depends upon the reaction components used and will in most cases preftreatment with a compound $R_1Z$ in which $R_1$ has the above meaning, and Z stands for a halogen atom, e.g. a bromine atom, or an alkyl- or arylsulphonyloxy group, or with a di-$R_1$-sulphate, a diazo derivative of the formula $R_1N_2$ or a quaternary derivative of the formula $R_1N^+(Alk)_3$, in which $R_1$ has the above meaning and Alk stands for alkyl with from 1 to 6 carbon atoms.

The compounds of the invention in which Y stands for S may also be prepared according to the following reaction scheme:

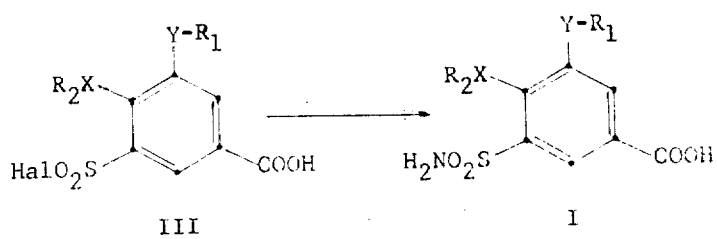

III        I in which formulae the substituents $R_1$, $R_2$, X, and Y are as defined before; and Hal stands for a halogen atom, preferably chlorine. The reaction is performed by treating the compound of formula III with ammonia, either with liquid ammonia or preferably concentrated aqueous ammonia, or under reaction conditions where ammonia is liberated, such as treatment with ammonium carbonate or hexamethylene tetramine, if necessary by heating. The isolation of the compounds of formula I can be performed by means of well-known standard procedures.

When esters of the compounds of the formula III are used in the reaction, the compounds of the formula I are obtained as esters, or in some cases due to an aminolysis as amides. The corresponding free acids may, optionally, be obtained by a subsequent saponification. In case of the desired product being an ester and the starting material of formula III being the free acid, an esterification can be performed either before or after the amidation process.

The starting compounds of formula III can be prepared as follows:

The well-known 4-chloro-3-chlorosulfonyl-5-nitrobenzoic acid is reduced, for instance by means of sodium sulphite in known manner to the corresponding sulfinic acid which is obtained as e.g. the mono sodium salt of 4-chloro-5-nitro-3-sulfinobenzoic acid. This compound is treated with a compound of the formula $R_2XH$, in which $R_2$ and X are as defined before, preferably by heating the components, if necessary in the presence of an acid binding agent, in a suitable solvent, or when appropriate, by using the compound $R_2XH$ as solvent. The reaction can be performed at room temperature or at elevated temperature up to about the boiling point of the solvent used. By this reaction the $R_2X$ radical replaces the 4-chloro atom whereafter the reaction product is isolated e.g. as the mono sodium salt of a 5-nitro-4-$R_2$X-3-sulfinobenzoic acid. The sulfinic acid group and the nitro group of these compounds are reduced throughout, e.g. with zinc and acids, such as hydrochloric acid, to the corresponding 5-amino-4-$R_2$X-3-mercaptobenzoic acid.

In order to obtain the corresponding 3-hydroxy-compound, a 3-amino-4-$R_2$X-5-nitrobenzoic acid, which is a known compound or can be produced analogous with the known compounds, is diazotized and the resulting diazonium group replaced by hydroxyl as generally known for the transformation of aromatic amines to hydroxy compounds, yielding a 3-hydroxy-4-$R_2$X-5-nitrobenzoic acid, in which the 5-nitro group is thereafter reduced, yielding the corresponding 5-amino-3-hydroxy-4-$R_2$X-benzoic acid.

The 5-amino-4-$R_2$X-3-YH-benzoic acids (Y = oxygen or sulphur) thus obtained are then alkylated, whereby the corresponding 3-$YR_1$- derivatives are obtained. This alkylation can be performed either on the free acid or on one of its salts or esters as described above in connection with the preparation of the starting materials of formula II.

The 5-amino-4-$R_2$X-3-$YR_1$-benzoic acids thus obtained are thereafter through their corresponding diazonium salts and by means of the well-known Meerwein-reaction transferred into the corresponding 5-halosulfonyl derivatives of the general formula III.

The compounds of the invention can further be prepared by an alkylation according to the following reaction scheme:

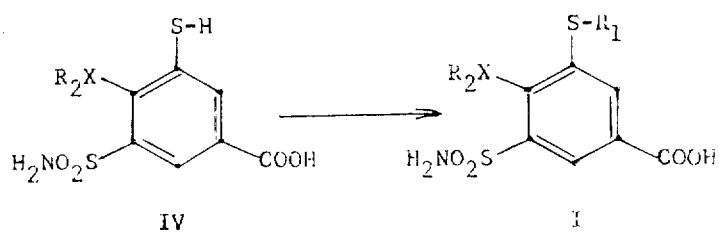

IV         I in which formulae the substituents $R_1$, $R_2$, and X are as defined before. This alkylation can be performed either on the free acid or on one of its salts or esters as described above in connection with the preparation of the starting materials of formula II. The isolation of the compounds of formula I can be performed by means of well-known standard procedures.

When esters of the compounds of the formula IV are used in the reaction, the compounds of the formula I are obtained as esters. The corresponding free acids may, optionally, be obtained by a subsequent saponification. In case of the desired product being an ester and the starting material of formula IV being the free acid, an esterification can be performed.

The starting compounds, 5-sulfamyl-4-$R_2$X-3-mercaptobenzoic acids, of formula IV can be prepared from 5-amino-4-$R_2$X-3-mercaptobenzoic acids, which are prepared as described above in connection with the preparation of the starting materials of formula III. These compounds are oxydized to their corresponding disulfides, i.e. 5,5'-diamino-3,3'-dicarboxy-6,6'-di-$R_2$X-diphenyl disulfides. These disulfides are thereafter through their corresponding diazonium salts and by means of the well-known Meerwein-reaction, transferred into the corresponding 5,5'-dihalosulfonyl disulfides. By treating these intermediates with ammonia, the corresponding 5,5'-disulfamyl disulfides are obtained. These 5,5'-disulfamyl-3,3'-dicarboxy-6,6'-di-$R_2$X-diphenyl disulfides are by treatment with dithionite or other suitable reducing agents transferred into the starting compounds of formula IV. If desired, esters of these compounds can be prepared by a simple esterification process before the compounds are subjected to the alkylation process according to the invention.

The reactions described above for the production of the starting materials of formula II, III, and IV are all well-known to the skilled chemist, and the reaction products are easily isolated.

The invention will now be illustrated by the following non-limiting Examples from which the details of the embodiments will be apparent.

EXAMPLE 1

4-Chloro-3-mercapto-5-sulfamylbenzoic acid

A stirred mixture of 3-amino-4-chloro-5-sulfamylbenzoic acid (40 g), concentrated hydrochloric acid (32 ml), water (100 ml), and ice (300 g) is diazotized by dropwise addition of a solution of sodium nitrite (11.5 g) in water (40 ml) during 30 minutes while stirring at 0° to 5° C. After additional stirring for 30 minutes at this temperature the reaction mixture is filtered, and the filtrate is during 30 minutes added dropwise to a stirred alkaline solution of sodium sulfide at 0° to 5° C. (The sodium sulfide solution is prepared previously from 42 g sodium sulfide ($Na_2S$, $9H_2O$), sulfur (5.5 g), and 3 N sodium hydroxide (75 ml) by mixing and heating to approximately 50° C.). After stirring for 18 hours the reaction mixture is adjusted to pH 3 by addition of concentrated hydrochloric acid while cooling. The precipitated disulfide is collected by filtration, washed with water and suspended in acetic acid (50 ml). The stirred suspension is thereafter boiled while zinc powder (5.5 g) is added in portions during 2 hours. After additional boiling for 2 hours the mixture is cooled to room temperature and filtered. The filtrate is acidified to pH 1.5 by addition of hydrochloric acid to precipitate the crude 4-chloro-3-mercapto-5-sulfamylbenzoic acid showing a melting point of 263° – 264° C. after recrystallization from ethanol.

EXAMPLE 2

3-Butylthio-4-chloro-5-sulfamylbenzoic acid

To a stirred solution of 4-chloro-3-mercapto-5-sulfamylbenzoic acid (5.5 g) in 1 N sodium hydroxide (29.5 ml), butyl iodide (2.1 ml) is added. After additional stirring for 50 hours precipitates the sodium salt of 3-butylthio-4-chloro-5-sulfamylbenzoic acid which is collected and washed with ice water. The sodium salt is suspended in water (25 ml) and 1 N hydrochloric acid added slowly until a pH value of 1. The precipitate is collected by filtration and recrystallized from aqueous ethanol to yield 3-butylthio-4-chloro-5-sulfamylbenzoic acid with a melting point of 202° – 203° C.

EXAMPLE 3

Ethyl 3-butylthio-4-chloro-5-sulfamylbenzoate 3-butyethio-4-chloro-5-sulfamylbenzoic acid (1.8 g) in a saturated solution of hydrogen chloride in ethanol (40 ml) is stirred for 18 hours. The precipitate is collected by filtration and washed with ethanol and petroleum ether to yield ethyl 3-butylthio-4-chloro-5-sulfamylbenzoate with a melting point of 160° – 162° C.

EXAMPLE 4

Ethyl 3-benzylthio-4-chloro-5-sulfamylbenzoate

By replacing the 3-butylthio-4-chloro-5-sulfamylbenzoic acid with 3-benzylthio-4-chloro-5-sulfamylbenzoic acid and by using the procedure described in example 3, ethyl 3-benzylthio-4-chloro-5-sulfamylbenzoate is obtained with a melting point of 182° – 182.5° C.

EXAMPLE 5

3-Benzylthio-4-chloro-5-sulfamylbenzoic acid

4Chloro-3-mercapto-5-sulfamylbenzoic acid (0.27 g) is dissolved in water (25 ml) by addition of 1 N sodium hydroxide until pH 8. Benzyl bromide (0.15 ml) is added and the reaction mixture stirred for 18 hours. Addition of 4 N hydrochloric acid until pH 1.5 precipitates a crude material which is collected by filtration, washed with water, and recrystallized from aqueous ethanol to yield 3-benzylthio-4-chloro-5-sulfamylbenzoic acid with a melting point of 241° – 242.5° C.

EXAMPLE 6

Ethyl-3-benzylthio-4-phenylthio-5-sulfamylbenzoate

A mixture of ethyl 3-benzylthio-4-chloro-5-sulfamylbenzoate (0.77 g), thiophenol (0.36 ml), and dry ethanol (15 ml) containing 3 millimoles of sodium thiophenolate is refluxed for 20 hours. After cooling the precipitate is collected by filtration to yield ethyl 3-benzylthio-4-phenylthio-5-sulfamylbenzoate with a melting point of 151°– 152° C.

EXAMPLE 7

3-Benzylthio-4-phenylthio-5-sulfamylbenzoic acid

A mixture of ethyl 3-benzylthio-4-phenylthio-5-sulfamylbenzoate (0.35 g), 1 N sodium hydroxide (10 ml), and ethanol (5 ml) is stirred for 10 minutes. The resulting solution is boiled for 2 minutes and is thereafter left for 1 hour to reach room temperature. 1 N hydrochloric acid (10.5 ml) is added to precipitate 3-benzylthio-4-phenylthio-5-sulfamylbenzoic acid. After collection by filtration and recrystallization from aqueous ethanol the compound is obtained with a melting point of 208° – 209° C.

EXAMPLE 8

3-Benzylsulfonyl-4-chloro-5-sulfamylbenzoic acid

A mixture of 3-benzylthio-4-chloro-5-sulfamylbenzoic acid (0.75 g), acetic acid (25 ml), and hydrogen peroxide (2 ml of an 30% aqueous solution) is stirred for 2 days at room temperature. Addition of water (100 ml) precipitates 3-benzylsulfonyl-4-chloro-5-sulfamylbenzoic acid. After collection by filtration and recrystallization from aqueous ethanol the compound crystallizing with one mole of water, is obtained with a melting point of 236° – 237° C.

EXAMPLE 9

3-Butylthio-4-phenylthio-5-sulfamylbenzoic acid

A mixture of ethyl 3-butylthio-4-chloro-5-sulfamylbenzoate (0.85 g), thiophenol (0.6 ml), and dry ethanol (25 ml) containing 5 millimoles of sodium thiophenolate is refluxed for 6 hours. After evaporation in vacuo 1 N sodium hydroxide (20 ml) and ethanol (10 ml) are added, and the mixture is refluxed for 15 minutes. After cooling and extraction with diethyl ether, 3-butylthio-4-phenylthio-5-sulfamylbenzoic acid is precipitated from the aqueous layer by addition of 4 N hydrochloric acid. The precipitate is collected by filtration and recrystallized from aqueous ethanol to yield the desired acid having a melting point of 192° – 193° C.

EXAMPLE 10

5-Amino-3-mercapto-4-phenoxybenzoic acid

A. Mono sodium salt of 4-chloro-5-nitro-3-sulfinobenzoic acid.

Sodium sulfite (20 g) is added to water (60 ml) and while stirring and keeping the temperature between 15° C and 20° C, 4-chloro-3-chlorosulfonyl-5-nitrobenzoic acid (16 g) is added in portions during 2 hours. The reaction mixture is kept at pH 8 by adding 2 N sodium hydroxide via an automatical end-point titrator. After the base consume has ceased, the mono sodium salt of 4-chloro-5-nitro-3-sulfinobenzoic acid is precipitated from the solution by addition of concentrated hydrochloric acid (40 ml) at 5° C. The acidic salt is collected by filtration, recrystallized from water (30 ml) and obtained with a melting point of 219° C (decomposition).

B. Mono sodium salt of 5-nitro-4-phenoxy-3-sulfinobenzoic acid.

A mixture of mono sodium salt of 4-chloro-5-nitro-3-sulfinobenzoic acid (13.3 g), sodium hydrogen carbonate (20 g), phenol (14 g), and water (100 ml) is heated to 85° C and kept at this temperature for 40 hours. Then the reaction mixture is extracted with diethyl ether, and the aqueous layer acidified with 4 N hydrochloric acid. The precipitated mono sodium salt of 5-nitro-4-phenoxy-3-sulfinobenzoic acid is collected by filtration and recrystallized from water, and dried in vacuo at 115° C. The acid is obtained with a melting point of 227° C (decomposition).

C. 5-Amino-3-mercapto-4-phenoxybenzoic acid.

Zinc powder (38 g) is added to a warm solution (70° C) of the mono sodium salt of 5-nitro-4-phenoxy-3-sulfinobenzoic acid (10 g) in ethanol (190 ml), and while stirring 5 N hydrochloric acid (190 ml) is added dropwise. The reaction mixture is kept under nitrogen for an additional 2 hours at 70° C. After cooling and filtration, the ethanol is distilled off in vacuo. After standing in a refrigerator for 16 hours, the precipitated material is collected by filtration and washed with concentrated hydrochloric acid (15 ml). This material is then suspended in water (300 ml) and the pH adjusted to 2 by addition of 2 N sodium hydroxide. The obtained crude 5-amino-3-mercapto-4-phenoxybenzoic acid is collected and recrystallized from aqueous ethanol. The acid is obtained with a melting point of 199°–200° C.

EXAMPLE 11

5-Amino-3-mercapto-4-phenylthiobenzoic acid

A. Mono sodium salt of 5-nitro-4-phenylthio-3-sulfinobenzoic acid.

A mixture of mono sodium salt of 4-chloro-3-nitro-5-sulfinobenzoic acid (18 g), sodium hydrogen carbonate (26 g), thiophenol (6 ml) and water (130 ml) is stirred at 85° C for 6 hours. After cooling, the reaction mixture is adjusted to pH 2 by addition of 2 N hydrochloric acid. The precipitated mono sodium salt of 3-nitro-4-phenylthio-5-sulfinobenzoic acid is collected by filtration, recrystallized from water and dried at 115° C in vacuo.

B. 5-Amino-3-mercapto-4-phenylthiobenzoic acid.

Zinc powder (32 g) is added to a warm solution (70° C) of the mono sodium salt of 5-nitro-4-phenylthio-3-sulfinobenzoic acid (11 g) in ethanol (220 ml), and while stirring, 5 N hydrochloric acid (220 ml) is added dropwise. The reaction mixture is stirred for additional 2 hours at 70°–80° C. After filtration the ethanol is distilled off in vacuo, and the reaction mixture adjusted to pH 2 by addition of concentrated sodium hydroxide. The mother liquor is decanted off and the resulting solid reaction product warmed on a steam-bath for 5 minutes after addition of 1 N sodium hydroxide (300 ml). After filtration and subsequent cooling, 5-amino-3-mercapto-4-phenylthiobenzoic acid is precipitated by addition of 4 N hydrochloric acid until pH 2. After collection and recrystallization from aqueous ethanol, the compound is obtained with a melting point of 173.5°–174° C.

EXAMPLE 12

5-Amino-4-(p-methoxyphenoxy)-3-mercaptobenzoic acid

A. Mono sodium salt of 4-(p-methoxyphenoxy)-5-nitro-3-sulfinobenzoic acid.

A mixture of mono sodium salt of 4-chloro-5-nitro-3-sulfinobenzoic acid (29 g), sodium hydrogen carbonate (30 g), p-methoxyphenol (25 g), and water (200 ml) is slowly heated to 80° C and kept at this temperature for 96 hours while stirring. After cooling, the reaction mixture is extracted twice with diethyl ether, and after addition of saturated sodium chloride solution (200 ml) the aqueous layer is adjusted to pH 1.5 by addition of concentrated hydrochloric acid. The precipitated mono sodium salt of 4-(p-methoxyphenoxy)-5-nitro-3-sulfinobenzoic acid is collected, dried in air at 20° C. and obtained with 3 moles of water of crystallization.

B. 5-Amino-4-(p-methoxyphenoxy)-3-mercaptobenzoic acid.

By replacing mono sodium salt of 4-(p-methoxyphenoxy)-5-nitro-3-sulfinobenzoic acid (12 g) for the mono sodium salt of 5-nitro-4-phenylthio-3-sulfinobenzoic acid (11 g) in Example 11B, 5-amino-4-(p-methoxyphenoxy)-3-mercaptobenzoic acid is obtained with a melting point of 182°–184° C.

EXAMPLE 13

5-Amino-3-mercapto-4-(p-methylphenylthio)benzoic acid

A. Mono sodium salt of 4-(p-methylphenylthio)-5-nitro-3-sulfinobenzoic acid.

By replacing p-methylthiophenol (12.5 g) for p-methoxyphenol in Example 12, step A, and following the procedure described, the mono sodium salt of 4-(p-methylphenylthio)-5-nitro-3-sulfinobenzoic acid is obtained. The compound is recrystallized from water, air-dried at 20° C, and thereby obtained with 2 moles of water of crystallisation.

B. 5-Amino-3-mercapto-4-(p-methylphenylthio)benzoic acid.

By replacing in Example 11, step B, the mono sodium salt of 4(p-methylphenylthiol)-5-nitro-3-sulfinobenzoic acid for the mono sodium salt of 5-nitro-4-phenylthio-3-sulfinobenzoic acid and following the procedure described, 5-amino-3-mercapto-4-(p-methylphenylthio)-benzoic acid is obtained with a melting point of 178°–182° C.

EXAMPLE 14

5-Amino-3-benzylthio-4-phenoxybenzoic acid

5-Amino-3-mercapto-4-phenoxybenzoic acid (0.53 g) is suspended in water (20 ml) and the pH is adjusted to 8 by addition of 1 N sodium hydroxide. Benzyl bromide (0.34 g) is added to the resulting solution, and the reaction mixture is stirred for 90 minutes at room temperature. By addition of 1 N hydrochloric acid until pH 2.5 the 5-amino-3-benzylthio-4-phenoxybenzoic acid precipitates. After collection by filtration, recrystallization from ethanol and drying in vacuo at 80° C, the compound is obtained with a melting point of 159°–161° C.

EXAMPLE 15

5-Amino-3-ethylthio-4-phenoxybenzoic acid

5-Amino-3-mercapto-4-phenoxybenzoic acid (2.6 g) is dissolved in water (100 ml) by addition of 1 N sodium hydroxide (20 ml). Ethyl iodide (3.2 g) is added, and the reaction mixture stirred for 2 hours at room temperature. After addition of ethanol (50 ml), 5-amino-3-ethylthio-4-phenoxybenzoic acid is precipitated by addition of 1 N hydrochloric acid until pH 2.5. After collection by filtration, recrystallization from aqueous ethanol and drying in vacuo at 80° C the compound is obtained with a melting point of 154°–155° C.

EXAMPLE 16

5-Amino-4-phenoxy-3-n-propylthiobenzoic acid

A mixture of 5-amino-3-mercapto-4-phenoxybenzoic acid (2.61 g), 1 N sodium hydroxide (20.5 ml), and n-propyl iodide (1.5 ml) is shaken in a sealed reaction flask for 30 hours. Thereafter 5-amino-4-phenoxy-3-n-propylthiobenzoic acid is precipitated by addition of 1 N hydrochloric acid to the reaction mixture until pH 2.5. After collection, recrystallization from aqueous ethanol and drying in vacuo at 80° C, the compound is obtained with a melting point of 136°–137.5° C.

EXAMPLE 17

5-Amino-3-n-butylthio-4-phenoxybenzoic acid

5-Amino-3-mercapto-4-phenoxybenzoic acid (5.22 g) is suspended in water (150 ml), 1 N sodium hydroxide is added until pH 8, and n-butyl iodide (7.4 g) is added to the resulting solution. The reaction mixture is stirred for 16 hours whereafter 5-amino-3-n-butylthio-4-phenoxybenzoic acid is precipitated by addition of 1 N hydrochloric acid until pH 2.5. After collection, recrystallization from aqueous ethanol, and drying in vacuo at 65° C, the compound is obtained with a melting point of 131°–132° C.

EXAMPLE 18

5-Amino-3-sec-butylthio-4-phenoxybenzoic acid

A mixture of 5-amino-3-mercapto-4-phenoxybenzoic acid (2.6 g), sodium hydrogen carbonate (2 g), saturated sodium hydrogen carbonate (100 ml), and sec.-butyl iodide (2.2 g) is stirred for 6 hours at 55° C. After cooling, 5-amino-3-sec.-butylthio-4-phenoxybenzoic acid is precipitated by addition of hydrochloric acid until pH 2.5. After collection, recrystallization from aqueous ethanol, and drying in vacuo at 80° C, the compound is obtained with a melting point of 157°–159° C.

EXAMPLE 19

5-Amino-3-isobutylthio-4-phenoxybenzoic acid

By replacing isobutyl iodide (4 g) for sec.-butyl iodide in Example 18, 5-amino-3-isobutylthio-4-phenoxybenzoic acid is obtained with a melting point of 148°–150° C.

EXAMPLE 20

5-Amino-3-n-pentylthio-4-phenoxybenzoic acid

A mixture of 5-amino-3-mercapto-4-phenoxybenzoic acid (5.2 g), n-pentyl bromide (5 ml), and 0.5 N sodium hydroxide is stirred at room temperature for 5 days. 5-Amino-3-n-pentylthio-4-phenoxybenzoic acid is precipitated by addition of 4 N hydrochloric acid (30 ml). After collection by filtration, recrystallisation from cyclohexane and drying, the compound is obtained from a melting point of 98° C.

EXAMPLE 21

5-Amino-3-isoamylthio-4-phenoxybenzoic acid

By replacing isoamyl iodide (3 g) for sec-butyl iodide in Example 18 and following the procedure described with the exception that the reaction mixture is kept under nitrogen, 5-amino-3-isoamylthio-4-phenoxybenzoic acid is obtained with a melting point of 132°–133° C.

EXAMPLE 22

3-Allylthio-5-amino-4-phenoxybenzoic acid

A solution of 5-amino-3-mercapto-4-phenoxybenzoic acid (2.6 g) in saturated sodium hydrogen carbonate (120 ml) is cooled to 4° C. While cooling and stirring, allyl bromide (1 g) is added, and the reaction mixture is kept under nitrogen. After additional stirring for 10 minutes, 3-allylthio-5-amino-4-phenoxybenzoic acid is precipitated by addition of hydrochloric acid until pH 3. After collection by filtration, recrystallisation from aqueous ethanol, and drying in vacuo, the compound is obtained with a melting point of 142°–143° C.

EXAMPLE 23

5-Amino-4-phenoxy-3-propargylthiobenzoic acid

A mixture of 5-amino-3-mercapto-4-phenoxybenzoic acid (2.6 g), propargyl bromide (1.2 g) and saturated sodium hydrogen carbonate (120 ml) is stirred for 1 hour at 55° C. Despite a partial precipitation of the sodium salt of 5-amino-4-phenoxy-3-propargylthiobenzoic acid on cooling, crude 5-amino-4-phenoxy-3-propargylthiobenzoic acid is precipitated by addition of hydrochloric acid until pH 2.5. The acid is collected by filtration and redissolved in boiling saturated sodium hydrogen carbonate (12 ml). After cooling, the precipitated sodium salt is collected by filtration. The salt is redissolved in hot water (40 ml), and 5-amino-4-phenoxy-3-propargylthiobenzoic acid precipitated by addition of 1 N hydrochloric acid until pH 2.5. After collection by filtration and recrystallisation from aqueous ethanol, the compound is obtained with a melting point of 167°–168° C.

EXAMPLE 24

5-Amino-3-benzylthio-4-(p-methoxyphenoxy)benzoic acid

5-Amino-4-(p-methoxyphenoxy)-3-mercaptobenzoic acid (2 g) is dissolved in 1 N sodium hydrogen carbonate (50 ml), and after addition of benzyl bromide (0.85 ml), the reaction mixture is stirred for 17 hours. After extraction twice with diethyl ether (25 ml), the aqueous layer is adjusted to pH 2 by addition of 4 N hydrochloric acid. The precipitated 5-amino-3-benzylthio-4-(p-methoxyphenoxy)-benzoic acid is collected and recrystallized from aqueous ethanol. After drying in vacuo at 80° C, the compound is obtained with a melting point of 158°–161° C.

EXAMPLE 25

5-Amino-3-benzylthio-4-phenylthiobenzoic acid

5-Amino-3-mercapto-4-phenylthiobenzoic acid (1.6 g) is dissolved in 1 N sodium hydrogen carbonate (50 ml), and after addition of benzyl bromide (0.7 ml), the reaction mixture is stirred for 20 hours. The resulting suspension of the sodium salt of the reaction product is adjusted to pH 2 by addition of 4 N hydrochloric acid. The precipitated 5-amino-3-benzylthio-4-phenylthiobenzoic acid is collected by filtration and recrystallized from aqueous ethanol to yield the compound with a melting point of 170.5°–172° C.

EXAMPLE 26

5-Amino-3-benzylthio-4-(p-methylphenylthio)benzoic acid

By replacing 5-amino-3-mercapto-4-(p-methylphenylthio)-benzoic acid (1.67 g) for 5-amino-3-mercapto-4-phenylthiobenzoic acid in Example 25 and following the procedure described, 5-amino-3-benzylthio-4-(p-methylphenylthio)-benzoic acid is obtained with a melting point of 177°–179° C.

EXAMPLE 27

5-Amino-4-phenoxy-3-(3-thienylmethylthio)benzoic acid

To a solution of 5-amino-3-mercapto-4-phenoxybenzoic acid (2.5 g) in 0.5 N sodium hydroxide (100 ml), a solution of 3-bromoethylthiophene (3.5 g in benzene (20 ml)) is added. The reaction mixture is stirred for 2 hours at room temperature. After extraction with additional benzene, the aqueous layer is acidified by addition of 4 N hydrochloric acid to precipitate 5-amino-4-phenoxy-3-(3-thienylmethylthio)benzoic acid. After collection by filtration, recrystallisation from aqueous ethanol and drying, the compound is obtained with a melting point of 153°–155° C.

EXAMPLE 28

3-Benzylthio-4-phenoxy-5-sulfamylbenzoic acid

A. 3-Benzylthio-5-chlorosulfonyl-4-phenoxybenzoic acid.

To a solution of 5-amino-3-benzylthio-4-phenoxybenzoic acid (1.4 g) in 0.5 N lithium hydroxide (8 ml), lithium nitrite (0.21 g) is added. The solution is added slowly to a mixture of acetic acid (10 ml) and concentrated hydrochloric acid (10 ml) while stirring and keeping the temperature at 2°–5° C. The resulting diazonium mixture is poured into acetic acid (20 ml), saturated with sulphur dioxide and containing copper chloride (0.2 g CuCl$_2$, 2 H$_2$O). The reaction mixture is allowed to reach room temperature while stirring. After cooling, the precipitated 3-benzyl thio-5-chlorosulfonyl-4-phenoxybenzoic acid is isolated by filtration, washed with aqueous acetic acid, and dried in vacuo at room temperature.

B. 3-Benzylthio-4-phenoxy-5-sulfamylbenzoic acid.
3-Benzylthio-5-chlorosulfonyl-4-phenoxybenzoic acid (0.6 g) is added to concentrated aqueous ammonia (10 ml). After 1 hour, the reaction mixture is heated on a steam-bath for 15 minutes, and crude 3-benzylthio-4-phenoxy-5-sulfamylbenzoic acid precipitated by addition of a 1 N hydrochloric acid until pH 2.5. The crude product is dissolved in aqueous sodium hydrogen carbonate by heating. After cooling, the precipitated sodium salt of 3-benzylthio-4-phenoxy-5-sulfamylbenzoic acid is collected by filtration. The salt is redissolved in hot water (20 ml) and 3-benzylthio-4-phenoxy-5-sulfamylbenzoic acid precipitated by addition of 1 N hydrochloric acid. After cooling and collecting by filtration, and drying in vacuo at 80° C, the compound is obtained with a melting point of 235°–236° C.

EXAMPLE 29

3-Ethylthio-4-phenoxy-5-sulfamylbenzoic acid

A. 5-Chlorosulfonyl-3-ethylthio-4-phenoxybenzoic acid.

To a solution of 5-amino-3-ethylthio-4-phenoxybenzoic acid (1.16 g) in 1 N sodium hydroxide (4 ml), sodium nitrite (0.28 g) is added. The solution is added slowly to a mixture of acetic acid (10 ml) and concentrated hydrochloric acid (10 ml) while stirring and keeping the temperature at 2°–5° C. The resulting diazonium mixture is poured into acetic acid (20 ml), saturated with sulphur dioxide and containing copper chloride (0.2 g CuCl$_2$, 2 H$_2$O). The reaction mixture is allowed to reach room temperature while stirring. After cooling, the precipitated 3-ethylthio-5-chlorosulfonyl-4-phenoxybenzoic acid is collected by filtration, washed with aqueous acetic acid, and dried in vacuo at room temperatures.

B. 3-Ethylthio-4-phenoxy-5-sulfamylbenzoic acid.
5-Chlorosulfonyl-3-ethylthio-4-phenoxybenzoic acid (1 g) is added to concentrated aqueous ammonia (20 ml) at 5°–10° C. After 30 minutes the reaction mixture is heated on a steam-bath for 1 hour while most of the excess of ammonia was allowed to distill off. After cooling, the precipitated ammonium salt of 3-ethylthio-4-phenoxy-5-sulfamylbenzoic acid is collected by filtration. The salt is dissolved in hot water (75 ml) and the solution acidified by addition of hydrochloric acid. After cooling, the precipitated 3-ethylthio-4-phenoxy-5-sulfamylbenzoic acid is collected by filtration and recrystallized from aqueous ethanol to yield the compound with a melting point of 225°–227° C after drying in vacuo at 80° C.

EXAMPLE 30

4-Phenoxy-3-n-propylthio-5-sulfamylbenzoic acid

A. 5-Chlorosulfonyl-4-phenoxy-3-n-propylthiobenzoic acid.

By replacing 5-amino-4-phenoxy-3-n-propylthiobenzoic acid (1.1 g) for 5-amino-3-ethylthio-4-phenoxybenzoic acid in Example 29A, 5-chlorosulfonyl-4-phenoxy-3-n-propylthiobenzoic acid is obtained.

B. 4-Phenoxy-3-n-propylthio-5-sulfamylbenzoic acid.
By replacing 5-chlorosulfonyl-4-phenoxy-3-n-propylthiobenzoic acid for 5-chlorosulfonyl-3-ethylthio-4-phenoxybenzoic acid in Example 29B, 4-phenoxy-3-n-propylthio-5-sulfamylbenzoic acid is obtained with a melting point of 209°–209.5° C.

EXAMPLE 31

3-n-Butylthio-4-phenoxy-5-sulfamylbenzoic acid

A. 3-n-Butylthio-5-chlorosulfonyl-4-phenoxybenzoic acid.

By replacing 5-amino-3-n-butylthio-4-phenoxybenzoic acid (1.27 g) for 5-amino-3-ethylthio-4-phenoxybenzoic acid in Example 29 A, 3-n-butylthio-5-chlorosulfonyl-4-phenoxybenzoic acid is obtained.

B. 3-n-Butylthio-4-phenoxy-5-sulfamylbenzoic acid.

By replacing 3-n-butylthio-5-chlorosulfonyl-4-phenoxybenzoic acid for 5-chlorosulfonyl-3-ethylthio-4-phenoxybenzoic acid in Example 29 B, 3-n-butylthio-4-phenoxy-5-sulfamylbenzoic acid is obtained with a melting point of 222°–224° C.

EXAMPLE 32

3-sec.-Butylthio-4-phenoxy-5-sulfamylbenzoic acid

A. 3-sec.-Butylthio-5-chlorosulfonyl-4-phenoxybenzoic acid.

By replacing 5-amino-3-sec.-butylthio-4-phenoxybenzoic acid for 5-amino-3-ethylthio-4-phenoxybenzoic acid in Example 29 A, 3-sec.-butylthio-5-chlorosulfonyl-4-phenoxybenzoic acid is obtained.

B. 3-sec.Butylthio-4-phenoxy-5-sulfamylbenzoic acid.

3-sec.-Butylthio-5-chlorosulfonyl-4-phenoxybenzoic acid (1 g) is added to concentrated aqueous ammonia (25 ml) at 5°–10° C. The reaction mixture is allowed to stand at room temperature for 16 hours, whereafter 3-sec.-butylthio-4-phenoxy-5-sulfamylbenzoic acid is precipitated by addition of 1 N hydrochloric acid until pH 2.5. After collection by filtration, recrystallization from aqueous ethanol and drying in vacuo at 80° C, the compound is obtained with a melting point of 192°–193° C.

EXAMPLE 33

3-Isobutylthio-4-phenoxy-5-sulfamylbenzoic acid

A. 3-Isobutylthio-5-chlorosulfonyl-4-phenoxybenzoic acid.

By replacing 5-amino-3-isobutylthio-4-phenoxybenzoic acid for 5-amino-3-ethylthio-4-phenoxybenzoic acid in Example 29 A, 3-isobutylthio-5-chlorosulfonyl-4-phenoxybenzoic acid is obtained.

B. 3-Isobutylthio-4-phenoxy-5-sulfamylbenzoic acid.

By replacing 3-isobutylthio-5-chlorosulfonyl-4-phenoxybenzoic acid for 3-sec.-butylthio-5-chlorosulfonyl-4-phenoxybenzoic acid in Example 32 B, 3-isobutylthio-4-phenoxy-5-sulfamylbenzoic acid is obtained with a melting point of 193°–194° C.

EXAMPLE 34

3-n-Pentylthio-4-phenoxy-5-sulfamylbenzoic acid

To a solution of 5-amino-3-n-pentylthio-4-phenoxybenzoic acid (1.33 g) in 1 N potassium hydroxide (4 ml), potassium nitrite (0.35 g) is added. The solution is added slowly in a mixture of acetic acid (10 ml) and concentrated hydrochloric acid (10 ml) while stirring and keeping the temperature at 2°–5° C. The resulting diazonium mixture is poured into acetic acid (20 ml), saturated with sulphur dioxide and containing copper chloride (0.2 g CuCl$_2$, 2 H$_2$O). The reaction mixture is allowed to reach room temperature while stirring. After cooling, the aqueous layer is decanted from the oily 5-chlorosulfonyl-3-n-pentylthio-4-phenoxybenzoic acid thus formed, and the oily product is dissolved in cooled concentrated aqueous ammonia (25 ml). The reaction mixture is left to stand at room temperature for 16 hours, whereafter 3-n-pentylthio-4-phenoxy-5-sulfamylbenzoic acid is precipitated by acidification with 4 N hydrochloric acid. After collection by filtration, recrystallisation from aqueous ethanol and drying, the compound is obtained with a melting point of 180°–182° C.

EXAMPLE 35

3-Isoamylthio-4-phenoxy-5-sulfamylbenzoic acid

A. 5-Chlorosulfonyl-3-isoamythio-4-phenoxybenzoic acid.

By replacing in Example 29A 5-amino-3-isoamylthio-4-phenoxybenzoic acid (1.33 g) for 5-amino-3-ethylthio-4-phenoxybenzoic acid and following the procedure described, 5-chlorosulfonyl-3-isoamylthio-4-phenoxybenzoic acid is obtained with a melting point of 168°–169° C.

B. 3-Isoamylthio-4-phenoxy-5-sulfamylbenzoic acid.

By replacing in Example 29B 5-chlorosulfonyl-3-isoamythio-4-phenoxybenzoic acid for 5-chlorosulfonyl-3-ethylthio-4-phenoxybenzoic acid and following the procedure described, the ammonium salt and the free acid of 3-isoamylthio-4-phenoxy-5-sulfamylbenzoic acid is provided. The acid is obtained with a melting point of 226°–227° C.

EXAMPLE 36

3-Allylthio-4-phenoxy-5-sulfamylbenzoic acid.

A. 3-Allylthio-5-chlorosulfonyl-4-phenoxybenzoic acid.

By replacing in Example 29A 3-allylthio-5-amino-4-phenoxybenzoic acid (1.2 g) for 5-amino-3-ethylthio-4-phenoxybenzoic acid and following the procedure described, 3-allylthio-5-chlorosulfonyl-4-phenoxybenzoic acid is obtained with a melting point of 160°–162° C.

B. 3-Allylthio-4-phenoxy-5-sulfamylbenzoic acid.

3-Allylthio-5-chlorosulfonyl-4-phenoxybenzoic acid (1 g) is dissolved in cooled concentrated aqueous ammonia (20 ml) while stirring. After 1 hour the reaction mixture is heated on steam bath for 5 minutes, cooled, and 3-allylthio-4-phenoxy-5-sulfamylbenzoic acid preciptitated by addition of 4 N hydrochloric acid. After collection by filtration, recrystallisation from aqueous ethanol, and drying, the compound is obtained with a melting point of 218°–219° C.

EXAMPLE 37

4-Phenoxy-3-propargylthio-5-sulfamylbenzoic acid

A. 5-chlorosulfonyl-4-phenoxy-3-propargylthiobenzoic acid.

By replacing in Example 29A 5-amino-4-phenoxy-3-propargylthiobenzoic acid (1.2 g) for 5-amino-3-ethylthio-4-phenoxybenzoic acid and following the procedure described, 5-chlorosulfonyl-4-phenoxy-3-propargylthiobenzoic acid is obtained with a melting point of 177°–179° C.

B. 4-Phenoxy-3-propargylthio-5-sulfamylbenzoic acid.

By replacing 5-chlorosulfonyl-4-phenoxy-3-propargylthiobenzoic acid for 5-chlorosulfonyl-3-allylthio-4-phenoxybenzoic acid in Example 36B and following the procedure described with the exception that the heating on a steam bath is extended to 3 hours, 4-phenoxy-3-propargylthio-5-sulfamylbenzoic acid is obtained with a melting point of 197°–198° C.

EXAMPLE 38

3-Benzylthio-4-(p-methylphenylthio)-5-sulfamylbenzoic acid

A. 3-Benzylthio-5-chlorosulfonyl-4-(p-methylphenylthio)-benzoic acid.

By replacing in Example 29A a solution of 5-amino-3-benzylthio-4-(p-methylphenylthio)benzoic acid (0.76 g) and sodium nitrite (0.15 g) in 0.2 N sodium hydroxide (10 ml) for the solution of 5-amino-3-ethylthio-4-phenoxybenzoic acid and sodium nitrite in 1 N sodium hydroxide and following the procedure described, 3-benzylthio-5-chlorosulfonyl-4-(p-methylphenylthio)benzoic acid is obtained with a melting point of 188°–190° C.

B. 3-Benzylthio-4-(p-methylphenylthio)-5-sulfamylbenzoic acid.

3-Benzylthio-5-chlorosulfonyl-4-(p-methylphenylthio)-benzoic acid (0.5 g) is added to concentrated aqueous ammonia (10 ml) while cooling and stirring. After 2 hours at room temperature, the reaction mixture is heated on a steam bath for 5 minutes, and after addition of ethanol (8 ml) the 3-benzylthio-4-(p-methylphenylthio)-5-sulfamylbenzoic acid is precipitated by addition of 4 N hydrochloric acid until pH 1.5. After cooling, the compound is collected by filtration, recrystallized twice from aqueous ethanol and air-dried at room temperature. The compound is obtained with a melting point of 250°–251° C. crystallizing with one mol of ethanol.

EXAMPLE 39

4-Phenoxy-5-sulfamyl-3-(3-thienylmethylthio)benzoic acid

A. 5-Chlorosulfonyl-4-phenoxy-3-(3-thienylmethylthio)-benzoic acid.

To a solution of 5-amino-4-phenoxy-3-(3-thienylmethylthio)benzoic acid (3.5 g) in 1 N potassium hydroxide (10 ml), potassium nitrite (0.85 g) is added. The solution is slowly added to a mixture of acetic acid (20 ml) and concentrated hydrochloric acid (20 ml) while stirring and keeping the temperature at 2°–5° C. The resulting diazonium mixture is poured into acetic acid (40 ml) saturated with sulphur dioxide and containing copper chloride (0.5 g $CuCl_2$, 2 $H_2O$). Gaseous sulphur dioxide is bubbled through the reaction mixture which is allowed to reach room temperature while stirring. After cooling, the precipitated 5-chlorosulfonyl-4-phenoxy-3-(3-thienylmethylthio)benzoic acid is collected by filtration, washed with aqueous acetic acid, and dried in vacuo at room temperature.

B. 4-Phenoxy-5-sulfamyl-3-(3-thienylmethylthio)-benzoic acid.

By replacing 5-chlorosulfonyl-4-pheonoxy-3-(3-thienylmethylthio)benzoic acid for 3-allylthio-5-chlorosulfonyl-4-phenoxybenzoic acid in Example 36B and following the procedure described, 4-phenoxy-5-sulfamyl-3-(3-thienylmethylthio)benzoic acid is obtained with a melting point of 222°–224° C.

EXAMPLE 40

3-Benzylthio-4-(p-methoxyphenoxy)-5-sulfamylbenzoic acid

A. 3-Benzylthio-5-chlorosulfonyl-4-(p-methoxyphenoxy)benzoic acid.

By replacing 5-amino-3-benzylthio-4-(p-methoxyphenoxy)benzoic acid (1.1 g) for 5-amino-3-ethylthio-4-phenoxybenzoic acid in Example 29 A and by using 3 ml of 1 N sodium hydroxide and 0.21 g of sodium nitrite, the 3-benzylthio-5-chlorosulfonyl-4-(p-methoxyphenoxy)benzoic acid is obtained.

B. 3-Benzylthio-4-(p-methoxyphenoxy)-5-sulfamylbenzoic acid.

By replacing 3-benzylthio-5-chlorosulfonyl-4-(p-methoxyphenoxy)-benzoic acid for 5-chlorosulfonyl-3-ethylthio-4-phenoxybenzoic acid in Examples 29 B, the 3-benzy(thio-4-(p-methoxyphenoxy)-5sulfamylbenzoic acid is obtained with a melting point of 215°–216° C after drying in vacuo at 80° C.

EXAMPLE 41

3-Benzylthio-4-phenylthio-5-sulfamylbenzoic acid

A. 3-Benzylthio-5-chlorosulfonyl-4-phenylthiobenzoic acid.

5-Amino-3-benzylthio-4-phenylthiobenzoic acid (1.1 g), acetic acid (10 ml), and concentrated hydrochloric acid (10 ml) is stirred and cooled to 5° C. At this temperature a concentrated solution of sodium nitrite (0.21 g) is added slowly while stirring. The resulting diazonium mixture is poured into acetic acid (20 ml), saturated with sulphur dioxide and containing copper chloride (0.2 g $CuCl_2$, 2 $H_2O$). The reaction mixture is allowed to reach room temperature while stirring. After 30 minutes, the precipitated 3-benzylthio-5-chlorosulfonyl-4-phenylthiobenzoic acid is collected, washed with aqueous acetic acid and dried in vacuo at room temperature.

B. 3-Benzylthio-4-phenylthio-5-sulfamylbenzoic acid.

By replacing 3-benzylamino-5-chlorosulfonyl-4-phenylthiobenzoic acid for 5-chlorosulfonyl-3-ethyl thio-4-phenoxybenzoic acid in Example 29 B, and by dissolving the resulting ammonium salt in hot aqueous ethanol (20 ml) instead of water, the 3-benzylthio-4-phenylthio-5-sulfamylbenzoic acid is obtained with a melting point of 208°–208.5° C.

EXAMPLE 42

3-Mercapto-4-phenoxy-5-sulfamylbenzoic acid

A. 5,5'-Diamino-3,3'-dicarboxy-6,6'diphenoxydiphenyl disulfide.

A mixture of 5-amino-3-mercapto-4-phenoxybenzoic acid (2.6 g), 1 N sodium hydroxide, and ethanol (25 ml) is heated to 50° C. Then a solution of iodine (1.27 g) in ethanol is added, while stirring. The reaction mixture is acidified by addition of 4 N hydrochloric acid and the 5,5-diamino-3,3'-dicarboxy-6,6'-diphenoxydiphenyl disulfide is precipitated by addition of water (100 ml). After collecting and washing with aqueous ethanol, the desired compound is obtained with a melting point of 282°–283° C.

B. 3,3'-Dicarboxy-5,5'-dichlorosulfonyl-6,6'-diphenoxydiphenyl disulfide.

To a solution of 5,5'-diamino-3,3'-dicarboxy-6,6'-diphenoxydiphenyl disulfide (2.6 g) in 1 N sodium hydroxide (10 ml), sodium nitrite (0.7 g) is added. The solution is added slowly to a mixture of acetic acid (15 ml) and concentrated hydrochloric acid (15 ml), while stirring and keeping the temperature at 2°–5° C. The resulting diazonium mixture is poured into acetic acid (30 ml) saturated with sulfur dioxide and containing copper chloride (0.3 g of $CuCl_2$, 2 $H_2O$). The reaction mixture is allowed to reach room temperature, while stirring. After additional stirring for 1 hour the precipitated 3,3'-dicarboxy-5,5'-dichlorosulfonyl-6,6'-diphenoxydiphenyl disulfide is collected by filtration, washed with aqueous acetic acid, and dried in vacuo at room temperature. The desired compound is obtained with a melting point of 225° C.

C. 3,3'-Dicarboxy-6,6'-diphenoxy-5,5'-disulfamyldiphenyl disulfide.

3,3'-Dicarboxy-5,5'-dichlorosulfonyl-6,6'-diphenoxydiphenyl disulfide (1 g) is added to liquid ammonia (10 ml) in portions during 15 minutes. Then the excess of ammonia is allowed to distill off, while keeping the reaction flask at room temperature. The residue is dissolved in water (10 ml) and the crude disulfide precipitated by acidification with 4 N hydrochloric acid. After collection and recrystallisation from ethanol the 3,3'-dicarboxy-6,6'-diphenoxy-5,5'-disulfamyldiphenyl disulfide is obtained in an analytically pure state.

D. 3-Mercapto-4-phenoxy-5-sulfamylbenzoic acid.

3,3'-Dicarboxy-6,6'-diphenoxy-5,5'-disulfamyldiphenyl disulfide (1.8 g) is dissolved in saturated sodium hydrogen carbonate (25 ml) after addition of additional sodium hydrogen carbonate (1 g). After addition of sodium dithionite (1 g) the reaction mixture is stirred at room temperature for 3 hours. Acidification by means of 4 N hydrochloric acid precipitated 3-mercapto-4-phenoxy-5-sulfamylbenzoic acid. The compound is collected and recrystallized from ethanol/water to yield the desired acid with a melting point of 205°–207° C.

EXAMPLE 43

3-n-Butylthio-4-phenoxy-5-sulfamylbenzoic acid

A. Sodium salt of 3-n-butylthio-4-phenoxy-5-sulfamylbenzoic acid

A mixture of 3-mercapto-4-phenoxy-5-sulfamylbenzoic acid (0.6 g), 1 N sodium hydrogen carbonate (25 ml), and n-butyl iodide (0.6 g) is stirred at 50° C. for 3 hours. After cooling, the precipitated sodium salt of 3-n-butylthio-4-phenoxy-5-sulfamylbenzoic acid is collected and washed with ice water. The compound crystallizes as a trihydrate.

B. 3-n-Butylthio-4-phenoxy-5-sulfamylbenzoic acid.

Sodium salt of 3-n-butylthio-4-phenoxy-5-sulfamylbenzoic acid (0.6 g) is dissolved in hot water (25 ml) and the free acid precipitated by acidification with 1 N hydrochloric acid. After cooling, the compound is collected by filtration and recrystallized from aqueous ethanol to yield 3-n-butylthio-4-phenoxy-5-sulfamylbenzoic acid with a melting point of 221°–223° C., after drying in vacuo at 80° C.

EXAMPLE 44

3-Benzylthio-4-phenoxy-5-sulfamylbenzoic acid

3-Mercapto-4-phenoxy-5-sulfamylbenzoic acid (0.6 g) is suspended in water (20 ml) and the pH is adjusted to 8 by addition of 1 N sodium hydroxide. Benzyl bromide (0.35 g) is added to the resulting solution, and the reaction mixture is stirred for 2 hours at room temperature. After cooling, the precipitated sodium salt of 3-benzylthio-4-phenoxy-5-sulfamylbenzoic acid is collected by filtration. The salt is dissolved in hot water (60 ml) and the solution acidified by addition of 1 N hydrochloric acid. After cooling, the precipitated 3-benzylthio-4-phenoxy-5-sulfamylbenzoic acid is collected by filtration and recrystallized from aqueous ethanol to yield the desired compound with a melting point of 234°–236° C., after drying in vacuo.

EXAMPLE 45

3-(2-Furylmethylthio)-4-phenoxy-5-sulfamylbenzoic acid

To a solution of 3-mercapto-4-phenoxy-5-sulfamylbenzoic acid (1.6 g) in diethylene glycol diethyl ether (15 ml), anhydrous potassium carbonate (0.5 g) and trimethylfurfurylammonium iodide (2 g) were added. The resulting mixture is stirred at 110° C. for 4 hours, cooled and poured into 0.3 N sodium hydroxide (75 ml). After extraction twice with diethyl ether, the aqueous layer is adjusted to pH 3 by addition of acetic acid. The reaction product is extracted with ethyl acetate, and the resulting organic solution is evaporated in vacuo. The residue is triturated with aqueous acetone giving rise to crystallisation. The 3-(2-furylmethylthio)-4-phenoxy-5-sulfamylbenzoic acid thus obtained is recrystallized from aqueous ethanol and dried. The compound is obtained with a melting point of 214°–216° C.

EXAMPLE 46

4-Phenoxy-3-(4-pyridylethylthio)-5-sulfamylbenzoic acid

A mixture of 3-mercapto-4-phenoxy-5-sulfamylbenzoic acid (1.7 g), sodium hydrogen carbonate (1 g), sodium dithionite (1 g), 4-vinylpyridine (0.8 ml) and saturated aqueous sodium hydrogen carbonate (17 ml) is stirred at 70° C. for 4 hours. After cooling, pH of the mixture is adjusted to 4.5 by addition of acetic acid. The precipitated material is collected by filtration, washed with water, and recrystallized from aqueous ethanol to yield 4-phenoxy-3-(4-pyridylethylthio)-5-sulfamylbenzoic acid.

EXAMPLE 47

Methyl 3-n-butylthio-4-phenoxy-5-sulfamylbenzoate

A mixture of 3-n-butylthio-4-phenoxy-5-sulfamylbenzoic acid (2.5 g) and methanol (75 ml) is saturated with gaseous hydrogen chloride. The reaction mixture is allowed to warm during saturation. After cooling and standing for 5 hours, the reaction mixture is evaporated in vacuo. The residue is triturated with water and sufficient sodium hydrogen carbonate to neutralize traces of hydrochloric acid. The precipitated methyl 3-n-butylthio-4-phenoxy-5-sulfamylbenzoate is collected and recrystallized from methanol/water to yield the ester with a melting point of 122°–123° C.

EXAMPLE 48

Methyl 4-phenoxy-5-sulfamyl-3-(3-thienylmethylthio)benzoate

By replacing in Example 47 4-phenoxy-5-sulfamyl-3-(3-thienylmethylthio)benzoic acid for 3-n-butylthio-4-phenoxy-5-sulfamylbenzoic acid and following the procedure described, methyl 4-phenoxy-5-sulfamyl-3-(3-thienylmethylthio)benzoate is obtained with a melting point of 148°–149° C.

Example 49

Cyanomethyl 3-n-butylthio-4-phenoxy-5-sulfamylbenzoate

A mixture of 3-n-butylthio-4-phenoxy-5-sulfamylbenzoic acid (2.3 g), chloroacetonitrile (1.4 g), triethylamine (0.61 g), and dry acetone (20 ml) is refluxed for 20 hours. After cooling the triethylamine hydrochloride formed is removed by filtration, and the filtrate is evaporated in vacuo. To the residue, water (35 ml) and ethylacetate (75 ml) are added, and the pH of the aqueous layer is adjusted to pH 7.5 by addition of 4 N hydrochloric acid. The organic layer is then separated, washed with diluted sodium hydrogen carbonate, dried and evaporated in vacuo. The residue is crystallized from chloroform petroleum ether to yield cyanomethyl 3-n-butylthio-4-phenoxy-5-sulfamylbenzoate with a melting point of 134°–135° C.

What we claim is:

1. A compound of the formula I

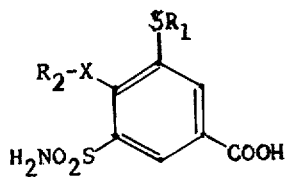

in which
- $R_1$ is selected from the group consisting of straight and branched $C_1$–$C_6$ alkyl, alkenyl and alkynyl radicals; said group further consisting of methyl and ethyl radicals monosubstituted with phenyl,
- $R_2$ stands for a phenyl radical, optionally being substituted with a member selected from the group consisting of lower alkyl, hydroxy and lower alkoxy;
- X stands for a member selected from the group consisting of oxygen and sulphur;

and pharmaceutically acceptable, non-toxic salts of the carboxylic acid of formula I; and esters thereof with cyanomethanol, benzyl alcohol, and $C_1$–$C_6$ alkanols.

2. A compound according to claim 1, in which $R_1$ stands for straight or branched $C_1$–$C_6$ alkyl, alkenyl or alkynyl; and $R_2$, and X have the meaning defined in claim 1.

3. A compound according to claim 1, in which $R_1$ stands for benzyl or phenethyl; and $R_2$, and X have the meaning defined in claim 1.

4. A compound as claimed in claim 1, in which $R_2$ stands for phenyl; and $R_1$, and X have the meaning defined in claim 1.

5. A compound as claimed in claim 1, in which $R_2$ stands for (lower alkyl)phenyl; and $R_1$, and X have the meaning defined in claim 1.

6. A compound as claimed in claim 1, in which $R_2$ stands for hydroxyphenyl; and $R_1$, and X have the meaning defined in claim 1.

7. A compound as claimed in claim 1, in which $R_2$ stands for (lower alkoxy)phenyl; and $R_1$, and X have the meaning defined in claim 1.

8. A compound as claimed in claim 1, in which X stands for oxygen; and $R_1$, and $R_2$ have the meanings defined in claim 1.

9. A compound as claimed in claim 1, in which X stands for sulphur; and $R_1$, and $R_2$ have the meanings defined in claim 1.

10. A compound as claimed in claim 1, in which $R_1$ stands for straight or branched $C_3$–$C_5$ alkyl; and $R_2$, and X have the meanings defined in claim 1.

11. A compound of formula I of claim 1, in which $R_1$ stands for straight or branched $C_3$–$C_5$ alkyl; $R_2$ stands for phenyl and X stands for oxygen or sulphur.

12. 3-Benzylthio-4-phenoxy-5-sulfamylbenzoic acid; and pharmaceutically acceptable, non-toxic salts thereof; and esters thereof with cyanomethanol, benzyl alcohol, and $C_1$–$C_6$ alkanols.

13. 3-n-Butylthio-4-phenylthio-5-sulfamylbenzoic acid; and pharmaceutically acceptable, non-toxic salts thereof; and esters thereof with cyanomethanol, benzyl alcohol, and $C_1$–$C_6$ alkanols.

14. 3-sec-Butylthio-4-phenoxy-5-sulfamylbenzoic acid; and pharmaceutically acceptable, non-toxic salts thereof; and esters thereof with cyanomethanol, benzyl alcohol, and $C_1$–$C_6$ alkanols.

15. 3Isobutylthio-4-phenoxy-5-sulfamylbenzoic acid; and pharmaceutically acceptable, non-toxic salts thereof; and esters thereof with cyanomethanol, benzyl alcohol, and $C_1$–$C_6$ alkanols.

16. 3-Benzylthio-4-p-methylphenylthio-5-sulfamylbenzoic acid; and pharmaceutically acceptable, non-toxic salts thereof; and esters thereof with cyanomethanol, benzyl alcohol, and $C_1$–$C_6$ alkanols.

17. 3-Benzylthio-4-p-methoxyphenoxy-5-sulfamylbenzoic acid; and pharmaceutically acceptable, non-toxic salts thereof; and esters thereof with cyanomethanol, benzyl alcohol, and $C_1$–$C_6$ alkanols.

18. 3-Benzylthio-4-phenylthio-5-sulfamylbenzoic acid; and pharmaceutically acceptable, non-toxic salts thereof; and esters thereof with cyanomethanol, benzyl alcohol, annd $C_1$–$C_6$ alkanols.

19. 3-n-Butylthio-4-phenoxy-5-sulfamylbenzoic acid; and pharmaceutically acceptable, non-toxic salts thereof; and esters thereof with cyanomethanol, benzyl alcohol, and $C_1$–$C_6$ alkanols.

20. 3-Ethylthio-4-phenoxy-5-sulfamylbenzoic acid; and pharmaceutically acceptable, non-toxic salts thereof; and esters thereof with cyanomethanol, benzyl alcohol, and $C_1$–$C_6$ alkanols.

21. 4-Phenoxy-3-n-propylthio-5-sulfamylbenzoic acid; and pharmaceutically acceptable, non-toxic salts thereof; and esters thereof with cyanomethanol, benzyl alcohol, and $C_1$–$C_6$ alkanols.

22. 3-n-Pentylthio-4-phenoxy-5-sulfamylbenzoic acid; and pharmaceutically acceptable, non-toxic salts thereof; and esters thereof with cyanomethanol, benzyl alcohol, and $C_1$–$C_6$ alkanols.

23. 3-Isoamylthio-4-phenoxy-5-sulfamylbenzoic acid; and pharmaceutically acceptable, non-toxic salts thereof; and esters thereof with cyanomethanol, benzyl alcohol, and $C_1$–$C_6$ alkanols.

24. 3-Allylthio-4-phenoxy-5-sulfamylbenzoic acid; and pharmaceutically acceptable, non-toxic salts thereof; and esters thereof with cyanomethanol, benzyl alcohol, and $C_1$–$C_6$ alkanols.

25. 4-Phenoxy-3-propargylthio-5-sulfamylbenzoic acid; and pharmaceutically acceptable, non-toxic salts thereof; and esters thereof with cyanomethanol, benzyl alcohol, and $C_1$–$C_6$ alkanols.

* * * * *